United States Patent [19]

Stewart

[11] 4,184,952
[45] Jan. 22, 1980

[54] MEASUREMENT OF BSW IN CRUDE OIL STREAMS

[75] Inventor: Thomas L. Stewart, Houston, Tex.

[73] Assignee: Shell Oil Company, Houston, Tex.

[21] Appl. No.: 905,261

[22] Filed: May 12, 1978

[51] Int. Cl.$^2$ .................... B01D 37/00; G01N 15/04
[52] U.S. Cl. .................................. 210/78; 73/61 R; 324/61 R; 324/65 R
[58] Field of Search .................. 210/78, 83, 84, 360 R, 210/360 A; 23/231, 258; 73/61.1 R, 53, 61 R, 61.4; 324/61 R, 65 R; 233/1 R

[56] References Cited

U.S. PATENT DOCUMENTS

| | | | |
|---|---|---|---|
| 3,140,257 | 7/1964 | Wilder et al. | 210/730 W |
| 3,677,071 | 7/1972 | Martin | 73/61.1 R |
| 3,771,353 | 11/1973 | Jenkins | 73/61.1 R |
| 4,055,986 | 11/1977 | Stewart et al. | 73/61.1 R |

Primary Examiner—Frank Sever

[57] ABSTRACT

To improve both the accuracy and reliability of capacitance-type basic sediment and water (BS&W) recorders, it is desirable to provide a clean, dry reference stream whose dielectric constant can be compared to that of a wet stream. This compensates for any variation in the physical composition of the fluid (e.g., pipeline crude oil) which might otherwise yield a false value for the BS&W content. In accordance with the present invention, the dry reference stream is provided by filtration and reverse centrifugation of part of the wet stream.

8 Claims, 2 Drawing Figures

MEASUREMENT OF BSW IN CRUDE OIL STREAMS

BACKGROUND OF THE INVENTION

The accuracy and reliability of basic sediment and water (BS&W) measurements as made by the capacitance-type recorders are dependent upon the extent to which the intrinsic dielectric constant of the subject fluid (e.g. pipeline crude oil) varies with time. The gravity and physical composition of crude oil are two factors which determine its intrinsic dielectric constant. Thus, if one or both of these properties should vary, the recorders measure the accompanying change in the dielectric constant as percent BS&W. This yields an inaccurate measurement of BS&W because the recorders must be initially set to read zero BS&W at the intrinsic dielectric constant of the fluid. The capacitor-type recorders of the prior art have no means for automatically correcting the zero BS&W setting to compensate for periodic variations in the oil properties mentioned.

Automatic compensation for erroneous BS&W measurements could be obtained if a clean, dry sample of the line fluid were continuously provided for measurement of its intrinsic dielectric constant. In this way the true BS&W content of the fluid could be measured by finding the difference between the dielectric constants of the wet and dry streams.

Automatic compensation has been delayed primarily because of the difficulty of designing an apparatus which would provide a continuous BS&W free sample from the line fluid. Some of the stringent requirements imposed upon the design and operation of such a unit are as follows: First, it must effect sufficient BS&W removal to yield a clean, dry effluent of less than approximately 0.01%V BS&W without altering the physical properties of the fluid. For this reason mechanical separation is mandatory; the use of demulsifiers is not acceptable. Second, it should be able to operate at normal line pressures, or at pressures higher than the bubble point of the most volatile component to eliminate cavitation. Third, it must be able to accommodate liquids having high as well as low viscosities, and liquids containing corrosive compounds. Fourth, it should be simple and economical in design and operation, virtually maintenance-free, and suitable for long-range and continuous service.

Providing a clean, dry, continuous reference stream without altering its physical composition is a difficult problem and the art has not been successful in this connection to date. Prior art considered pertinent to the present invention includes U.S. Pat. Nos. 3,546,926 and 3,189,180.

SUMMARY OF THE INVENTION

Figure 1:
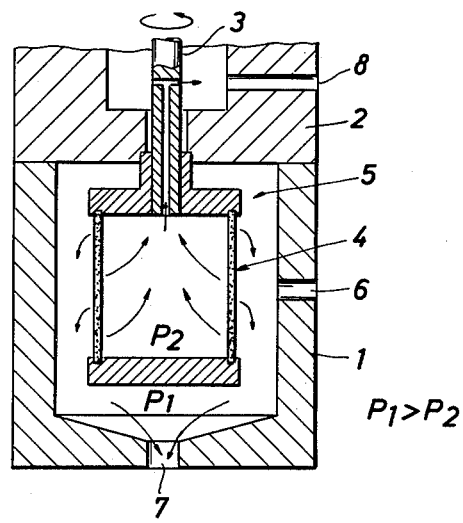
FIG. 1 is a schematic diagram of an emulsion separator.

The present invention provides a process and apparatus for separating a fluid containing at least two liquids of different densities by rotating a fluid pervious inner chamber within an outer chamber, admitting the fluid to the outer chamber, pressuring the fluid from the outer chamber into the inner chamber, allowing centrifugal force in the inner chamber to force more dense fluid back into the outer chamber, and separately withdrawing less-dense fluid from the inner chamber. The inner chamber is a filter and the fluid contains particles too large to pass through the filter.

Preferably, the process involves continuously measuring the water and sediment content (BS&W) of flowing crude oil having a varying intrinsic dielectric constant. The dielectric constant of a clean, dry sample of crude oil produced by the above process and apparatus is compared with the dielectric constant of the corresponding sample containing BS&W to determine the true BS&W content of the crude oil.

DESCRIPTION OF PREFERRED EMBODIMENTS

In accordance with the present invention, a water/oil emulsion separator is provided which is enclosed by a separator chamber housing 1 affixed to a bearing and seal housing 2 by bolts (not shown). Ball bearings and a mechanical seal (not shown) position a hollow drive shaft 3 within the bearing and seal housing. The hollow drive shaft is terminated at one end by a porous filter (e.g. stainless steel filter) which resides in a chamber 5 formed by housing 1 and containing oil/water emulsion which is admitted thereinto through emulsion inlet port 6. When the apparatus is in operation, underflow emulsion exits from chamber 5 via port 7 as shown by the direction of the downward arrows. Oil passes through the porous filter 4 into the hollow drive shaft 3 and exits via clean oil exit 8 as shown by the direction of the upward arrows. The hollow drive shaft 3 rotates the porous filter to break entering oil/water emulsion into oil and water which is spun out. Emulsion in chamber 5 is at a greater pressure than clean oil in port 8 which is filtered by passing through filter 4 and centrifuged inside the filter. Accordingly, it is apparent that the dry, clean oil stream exiting via port 8 is a product of both filtration and reverse centrifugation.

The fluid stream entering via port 6 containing emulsified water and suspended sediment is forced into the housing 1 at a flow rate which can be varied from approximately 0 to 5,000 ml per minute or more. Total flow of the wet stream, as well as flow of dry stream, are both related to physical size of the device. Permissible flow of the dry stream is proportional to the filter area, radius, and RPM squared. Flow of the wet stream is limited only by the piping and port sizes and the cross-sectional area of the annulus. The influx may be directed tangential to and opposing the direction of rotation of the porous filter 4. This condition creates a continuous additional shear force upon the outer surface of the filter, which aids in preventing particles from accumulating on and clogging the filter. In addition, the centrifugal force due to the high angular velocity of the filter forces the denser particles (water and sediment) outward toward the wall of the housing 1 and down through the underflow exit 7. The pressure differential between the housing and the inside of the filter tends to force the resident fluid through the filter pores and up through the hollow drive shaft 3 wherefrom it is discharged via port 8 to a dry oil chamber (not shown).

Figure 2:
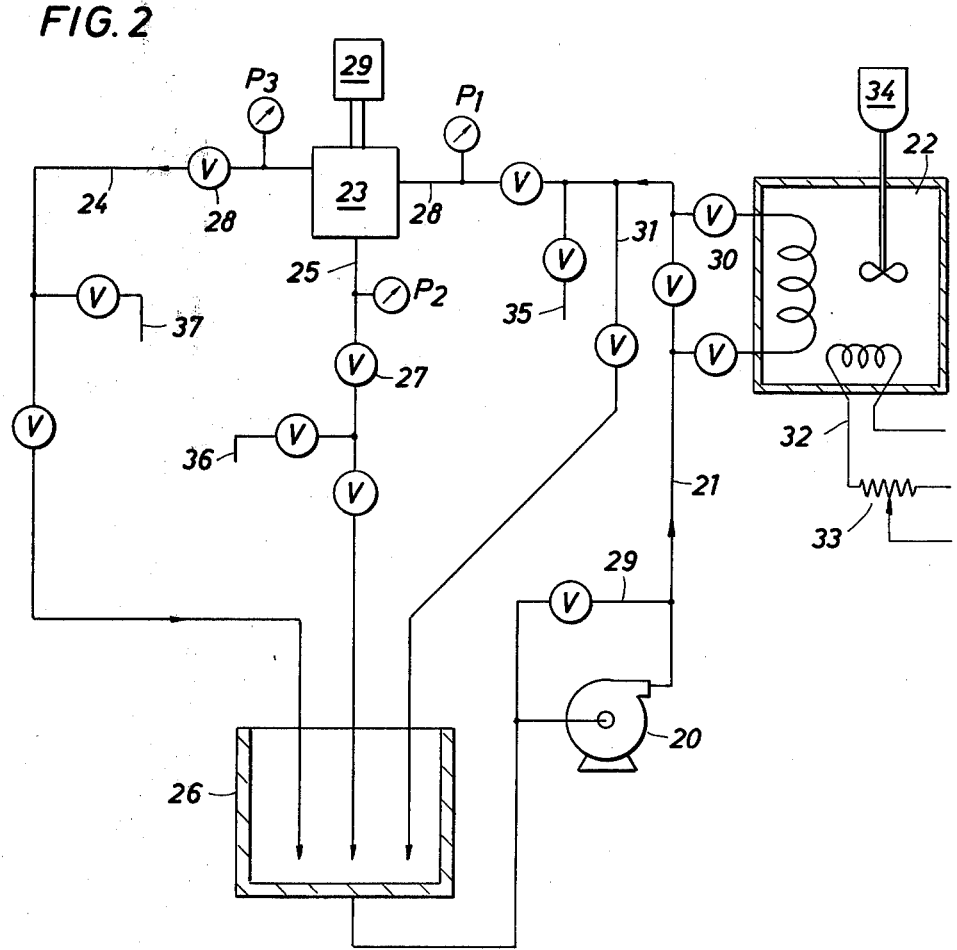
FIG. 2 is a flow diagram for a separator circuit.

The separator and its flow circuit as shown in FIG. 2 are designed to test certain variables and the effect to the variations upon separation efficiencies. Among these variables are speed of rotation of filter 4, width of annulus between filter 4 and housing 1, filter pore size, pressure differential between housing 1 and the interior of filter 4, entrance flow rate at port 6, direction of the influx emulsion through port 6, and temperature and viscosity of the influx emulsion. Several types of filters are available which are suitable for use with the invention. Specifically acceptable for use is a 20 micron pore filter manufactured by AMF CUNO as item number 50387-01-41-0201. The pore size of such filters ranges about 2 to about 55 microns or more. The annulus width between the filter and housing can vary from almost nil to about several inches or more, while the pressure differential between the housing and interior of the filter may vary from almost nil to about 70 psi or more. Differential pressure required is determined by centrifugal force and the resistance imposed by the filter and is limited by the physical strength of the filter to withstand high differential pressures. Entrance flow rates range from down to almost 0 to 50,000 ml/min or more while temperature of the influx emulsion varies from about 0° C. to about 40° C. or more. Viscosity of the influx emulsion varies from about 1 CS to about 50 CS or more. The speed of rotation of the filter ranges from about 100 rpm or less to 10,000 rpm or more. Preferably, the filter is rotated by an electric motor with a continuous range of variable speed drive for test purposes.

Testing described hereinafter was carried out with the separator shown in FIG. 1 and incorporated into the flow circuit shown in FIG. 2. A centrifugal pump 20 continuously circulated a sample fluid 21 through a heat exchanger 22 and separator housing 23. Wet oil 24 and dry oil effluents 25 were directed back to an emulsion reservoir 26. Pressure in separator 23 was maintained and varied by adjusting valve 27 at the dry oil underflow exit and valve 28 at the wet oil overflow exit. Rotational velocity of the filter within housing 2 was controlled by means of an expanding pulley, variable speed drive motor 29. The motor was calibrated for RPM versus control setting by means of a strobe light.

Pressures were measured by means of gages $P_1$, $P_2$, and $P_3$ located as close as possible to the inlet and outlet orifices. Flow rates were determined by measuring the volume of liquid discharged into a graduated cylinder per minute. Influx temperature was measured by a thermometer which was inserted in the influx emulsion line 28 close to the housing 23 entrance.

By pass lines 29, 30 and 31 were provided, respectively, about pump 20, heat exchanger 22 and separator 23. Heat exchanger 22 was heated by a heater 32 controlled by a rheostat 33 and was stirred by an electric stirrer 34.

All samples were drawn from tap 35, also used to check the flow rate of the influx emulsion, tap 36, also used to check the flow rate of the dry oil effluent, and tap 37, also used to check the flow rate of the efflux overflow. Following a change in any parameter such as RPM, flow rate, etc., ample time was allowed for the system to reach steady conditions before any samples were taken.

Samples to be analyzed for BS&W content were collected in 100 ml, ASTM approved, conical centrifuge tubes. In tests involving crude oil, the method of analysis prescribed by ASTM D-96 was used except that in addition a general demulsifier, Tretolite F-46, which is a surface-active chemical that enhances the agglomeration of small water droplets in oil into larger droplets, was added to the sample before centrifugation. Tests revealed that the results were identical for mineral oil-Kerosene samples regardless of whether the ASTM D-96 method was applied.

During each run the following measurable quantities were determined: $P_1$, $P_2$, and $P_3$, dry oil flow rate, total influx flow rate, influx temperature, RPM, and influx and dry oil BS&W content.

The filtration separation efficiency was defined as the percentage of BS&W removed:

$$\text{Efficiency} = \frac{(BS\&W)\text{in} - (BS\&W)\text{out}}{(BS\&W)\text{in}} \times 100$$

where (BS&W) in is the wet oil basic sediment and water and (BS&W) out is the dry oil BS&W.

All viscosities were reported as the viscosity of clean, dry oil. Emulsion viscosities were not determined experimentally due to the tendency for the water and sediment to coalesce and settle out while the sample was in the viscometer. Viscosity of dilute water-in-oil emulsions was determined from $$N' = N_e \left\{ 1 + 2.5 \phi \frac{\left(N_1 + \frac{2}{5} N_e\right)}{N_i + N_e} \right\}$$

where
 $N'$ = viscosity of emulsion
 $N_i$ = viscosity of internal phase (water)
 $N_e$ = viscosity of external phase (oil)
 $\phi$ = volume fraction of water emulsified This formula is accurate for $\phi = 0.025$. For most cases, the viscosities of the pure oil and the emulsion vary about 5% for a water content of $\phi = 0.02$. Two different types of oil were utilized in these experiments. The initial series of experiments were made using a 3:2 mixture by volume of mineral oil and deodorized kerosene. The properties of this oil are shown in Table 1. A sour West Texas crude sample was obtained from the Pasadena Terminal of the Rancho Pipe Line System. The physical properties of this oil are also shown in Table 1.

Results of the tests are shown in Table 2. In general, better separation was obtained at lower oil viscosities. Also, better separation was obtained with a finer filter, but RPM still is the principal governing factor.

TABLE I

OIL PROPERTIES

A. 3 volumes mineral oil to 2 volumes kerosene
Density    120° F. 39.0° API

| TEMPERATURE ° F. | VISCOSITY CENTISTOKES |
|---|---|
| 60 | 27.5 |
| 80 | 17.5 |
| 100 | 12.0 |
| 120 | 8.6 |

B  Rancho sour crude
Density    77° F., 35.0° API

| TEMPERATURE °F. | VISCOSITY CENTISTOKES |
|---|---|
| 60 | 14.7 |
| 80 | 9.7 |
| 100 | 7.2 |
| 120 | 5.1 |

TABLE 2

CORRELATION BETWEEN SEPARATION EFFICIENCY AND FLOW RATE USING MINERAL OIL - KEROSENE MIXTURE
FILTER POROSITY - 22μ
OIL VISCOSITY - 24.0 CENTISTOKES

| PRESSURES PSIG | | | | DRY OIL FLOW | INFLUX | DRY OIL | SEPARATION EFFICIENCY |
|---|---|---|---|---|---|---|---|
| $P_1$ | $P_2$ | $P_3$ | $-P_{1-3}$ PSI | RATE, CC/MIN. | BS&W, % | BS&W %V | % BS&W REMOVER |
| at 1,000 RPM Relative Centrifugal Force = 43 | | | | | | | |
| 7.8 | 7.5 | 3.3 | 4.5 | 960 | 1.70 | 1.45 | 15 |
| 9.3 | 8.7 | 7.5 | 1.8 | 65 | 1.50 | 0.20 | 87 |
| at 2,000 RPM, Relative Centrifugal Force = 170 | | | | | | | |
| 8.5 | 7.3 | 1.8 | 6.7 | 700 | 1.85 | 0.80 | 67 |
| 9.8 | 8.3 | 5.3 | 4.5 | 85 | 2.20 | 0.13 | 94 |
| Oil Viscosity - 14.5 Centistokes | | | | | | | |
| at 1,000 RPM, Relative Centrifugal Force = 43 | | | | | | | |
| 7.7 | 6.5 | 2.3 | 5.4 | 1,340 | 2.10 | 1.50 | 29 |
| 9.5 | 8.5 | 7.5 | 2.0 | 70 | 1.80 | 0.27 | 85 |
| at 2,000 RPM, Relative Centrifugal Force = 170 | | | | | | | |
| 8.5 | 7.0 | 1.3 | 7.2 | 900 | 2.10 | 0.75 | 64 |
| 10.0 | 8.5 | 5.5 | 4.5 | 100 | 2.20 | 0.10 | 96 |
| Oil Viscosity - 0.8 Centistokes | | | | | | | |
| at 1,000 RPM, Relative Centifugal Force = 43 | | | | | | | |
| 8.0 | 7.0 | 3.3 | 4.7 | 1,260 | 1.90 | 1.00 | 42 |
| 9.8 | 8.3 | 7.8 | 2.0 | 80 | 2.20 | 0.15 | 93 |
| at 2,000 RPM Relative Centrifugal Force = 170 | | | | | | | |
| 8.8 | 6.5 | 7.8 | 7.8 | 960 | 2.80 | 0.40 | 83 |
| 10.3 | 7.5 | 4.8 | 4.8 | 100 | 2.20 | 0.07 | 97 |
| Filter Porosity - 12 | | | | | | | |
| Oil Viscosity - 8.6 Centistokes | | | | | | | |
| at 1,000 RPM, Relative Centrifugal Force = 43 | | | | | | | |
| 8.8 | 7.5 | 3.3 | 5.5 | 1,800 | 2.00 | 1.0 | 50 |
| 10.3 | 9.3 | 8.5 | 1.8 | 100 | 1.90 | 0.05 | 97 |
| at 2,000 RPM, Relative Centrifugal Force = 170 | | | | | | | |
| 9.5 | 7.0 | 1.5 | 8.0 | 1,000 | 2.10 | 0.25 | 88 |
| 11.0 | 8.5 | 7.0 | 4.0 | 200 | 2.00 | 0.025 | 99 |
| Using Rancho Sour Crude (Low BS&W) | | | | | | | |
| Oil Viscosity - 7.5 Centistokes | | | | | | | |
| API Gravity at T° F. = 35.0 | | | | | | | |
| at 2,000 RPM, Relative Centrifugal Force = 170 | | | | | | | |
| 11.7 | 9.5 | 1.8 | 9.9 | 1,100 | 0.70 | 0.50 | 29 |
| 13.0 | 10.3 | 8.0 | 5.0 | 130 | 0.66 | 0.05 | 92 |
| 13.3 | 9.7 | 3.0 | 8.8 | 900 | 3.00 | 2.60 | 13 |
| 12.8 | 10.8 | 8.0 | 4.8 | 100 | 3.20 | 0.70 | 78 |

What I claim as my invention is:

1. A process for measuring the water and sediment content of flowing crude oil having a varying intrinsic dielectric constant comprising, continuously removing a sample stream of the crude oil, feeding the sample stream into an outer chamber containing an inner chamber having a wall formed of a filter, rotating the inner chamber while pressuring the sample from the outer chamber into the inner chamber, filtering sediment from the sample passing into the inner chamber and allowing centrifugal force in the inner chamber to force water in the sample back into the outer chamber, withdrawing clean dry sample from the inner chamber, and continuously measuring the difference between the dielectric constants of the sample and the clean dry sample to facilitate determining the true water and sediment content of the crude oil.

2. The process of claim 1 wherein the filter has porosity of from 2 to 55 microns or more.

3. The process of claim 2 wherein the inner chamber is rotated at from 100 to 10,000 rpm.

4. The process of claim 1 wherein the clean, dry sample fluid is withdrawn through a hollow drive shaft which rotates the inner chamber.

5. The process of claim 1 wherein the sample is introduced into the outer chamber at any angle between radially and approximately tangentially to the inner chamber.

6. The process of claim 5 wherein the direction of flow of the fluid, when introduced into the outer chamber, may either oppose or go with the direction of rotation of the inner chamber.

7. The process of claim 6 wherein the flow rate of the fluid varies up to 5,000 milliliters per minute.

8. The process of claim 1 wherein the pressure differential between the inner and outer chambers varies up to 70 psi.

* * * * *